United States Patent
Karp et al.

(10) Patent No.: US 6,814,938 B2
(45) Date of Patent: Nov. 9, 2004

(54) NON-PLANAR MICROFLUIDIC DEVICES AND METHODS FOR THEIR MANUFACTURE

(75) Inventors: Christoph D. Karp, Pasadena, CA (US); Stephen D. O'Connor, Pasadena, CA (US); Vincent K. Gustafson, Los Angeles, CA (US)

(73) Assignee: Nanostream, Inc., Pasadena, CA (US)

( * ) Notice: Subject to any disclaimer, the term of this patent is extended or adjusted under 35 U.S.C. 154(b) by 610 days.

(21) Appl. No.: 09/864,610

(22) Filed: May 23, 2001

(65) Prior Publication Data

US 2002/0177238 A1 Nov. 28, 2002

(51) Int. Cl.⁷ .......................... B01L 3/02; B01L 11/00; G01N 21/00; G01N 31/00; G01N 33/00
(52) U.S. Cl. .......................... 422/100; 422/50; 422/55; 422/58; 422/61; 422/63; 422/68.1; 422/81; 422/101; 422/102; 422/103; 422/104; 436/43; 436/52; 436/53
(58) Field of Search .................... 436/43, 52, 53; 422/50, 55, 58, 61, 63, 68.1, 81, 100, 101, 102, 103, 104

(56) References Cited

U.S. PATENT DOCUMENTS

| | | | |
|---|---|---|---|
| 4,313,440 A * | 2/1982 | Ashley | 604/191 |
| 4,868,129 A | 9/1989 | Gibbons et al. | 436/179 |
| 5,030,418 A | 7/1991 | Miyata | 422/63 |
| 5,478,526 A | 12/1995 | Sakai et al. | 422/81 |
| 5,698,299 A | 12/1997 | Schmidt et al. | 428/209 |
| 5,837,199 A | 11/1998 | Dumschat | 422/68.1 |
| 5,932,799 A | 8/1999 | Moles | 73/53.01 |
| 6,129,973 A | 10/2000 | Martin et al. | 428/166 |
| 6,264,892 B1 | 7/2001 | Kaltenbach et al. | 422/68.1 |
| 6,481,453 B1 * | 11/2002 | O'Connor et al. | 137/15.04 |
| 6,494,230 B2 | 12/2002 | Chow | 137/827 |
| 6,494,614 B1 | 12/2002 | Bennett et al. | 366/336 |
| 6,536,477 B1 * | 3/2003 | O'Connor et al. | 137/833 |
| 6,537,506 B1 | 3/2003 | Schwalbe et al. | 422/130 |
| 6,599,436 B1 | 7/2003 | Matzke et al. | 216/24 |
| 6,676,835 B2 * | 1/2004 | O'Connor et al. | 210/542 |

FOREIGN PATENT DOCUMENTS

| | | |
|---|---|---|
| AT | 391 634 B | 5/1988 |
| DE | 195 46 535 A1 | 12/1995 |
| WO | WO 98/54941 | 12/1998 |
| WO | WO 99/19717 | 4/1999 |
| WO | WO 99/29497 | 6/1999 |
| WO | WO 99/60397 | 11/1999 |
| WO | WO 99/65664 | 12/1999 |
| WO | WO 00/21659 | 4/2000 |

OTHER PUBLICATIONS

McDonald, et al., *Fabrication of microfluidic systems in poly(dimethylsiloxane)*, "Electrophoresis," 2000, No. 21, Wiley–VCH Verlag GmbH, 69451 Weinheim, 2000, pp. 27–40.

* cited by examiner

Primary Examiner—Robert J. Warden, Sr.
Assistant Examiner—Brian J. Sines
(74) Attorney, Agent, or Firm—Vincent K. Gustafson; Michael F. Labbee

(57) ABSTRACT

Non-planar microfluidic devices and methods for transferring fluids between vessels and microfluidic devices are provided. The devices may be contoured to physically contact non-planar vessels, such as pipes, tubes, vials, or syringes to establish fluid communication between a vessel and a microfluidic device. Devices according to the invention may be constructed from flexible, rigid, or combinations of flexible and rigid materials. In certain embodiments, microfluidic devices are composed of sandwiched stencils, and self-adhesive tapes may be used for one or more layers. A microfluidic device may be removably attached to a vessel with a non-permanent adhesive or adhesive layer. Continuously wrapped microfluidic devices fashioned from a single layer, in addition to rewindable microfluidic devices constructed from multiple layers, are provided. A multi-plunger syringe permits a microfluidic device or other reservoir coupled to the vessel to be filled on the draw stroke of the syringe plunger.

52 Claims, 12 Drawing Sheets

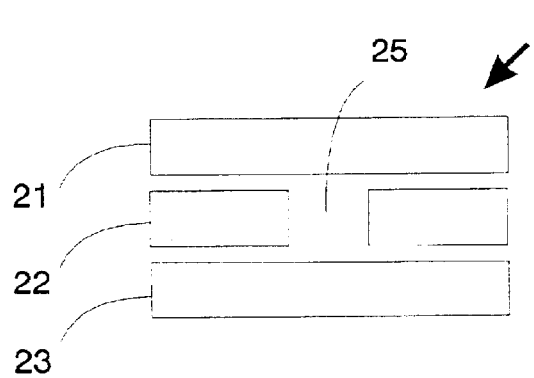 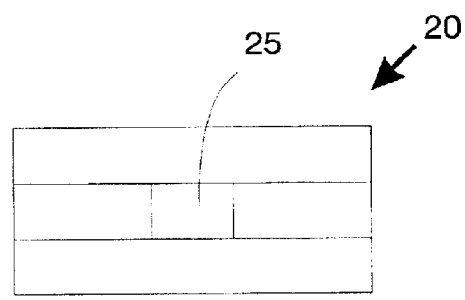
FIG. 2A  FIG. 2B
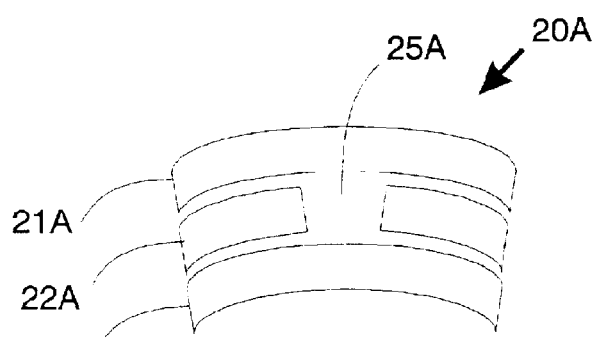 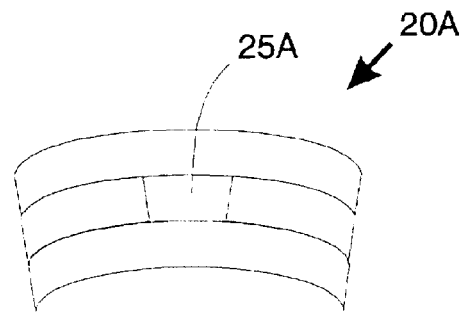
FIG. 2C  FIG. 2D
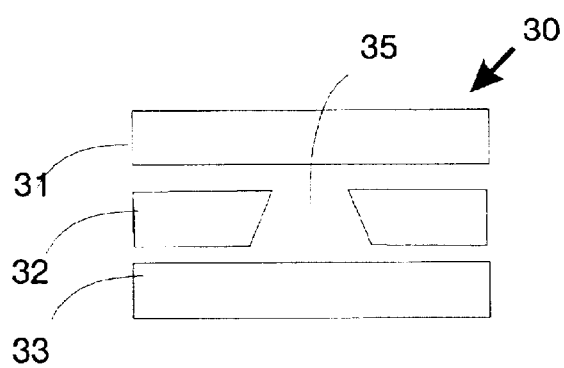 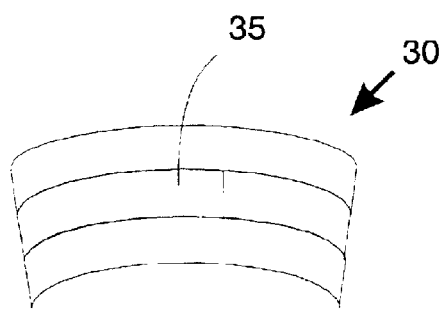
FIG. 2E  FIG. 2F

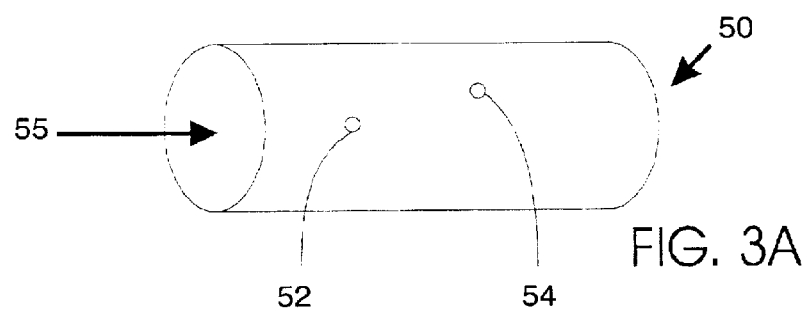
FIG. 3A
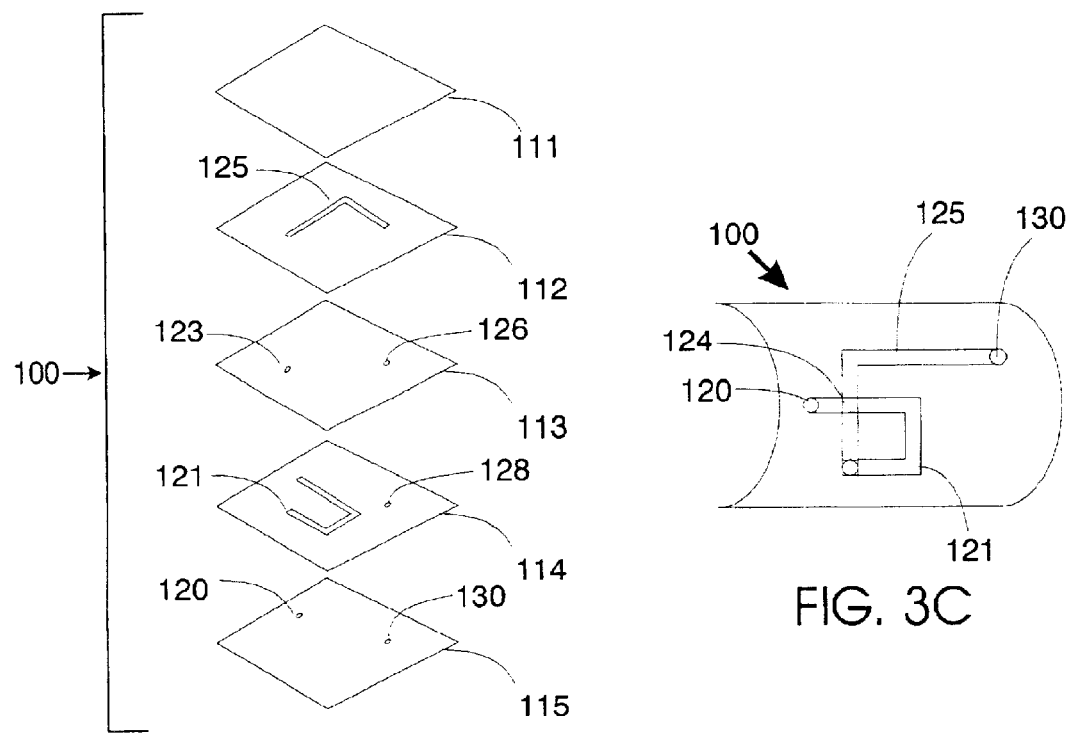
FIG. 3B
FIG. 3C
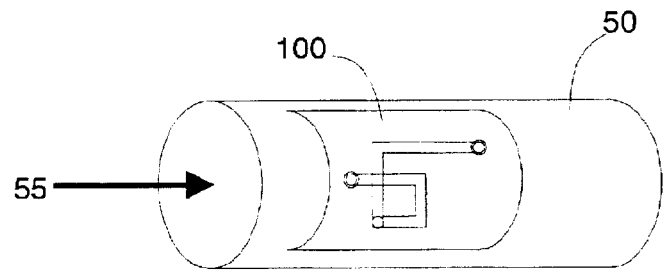
FIG. 3D

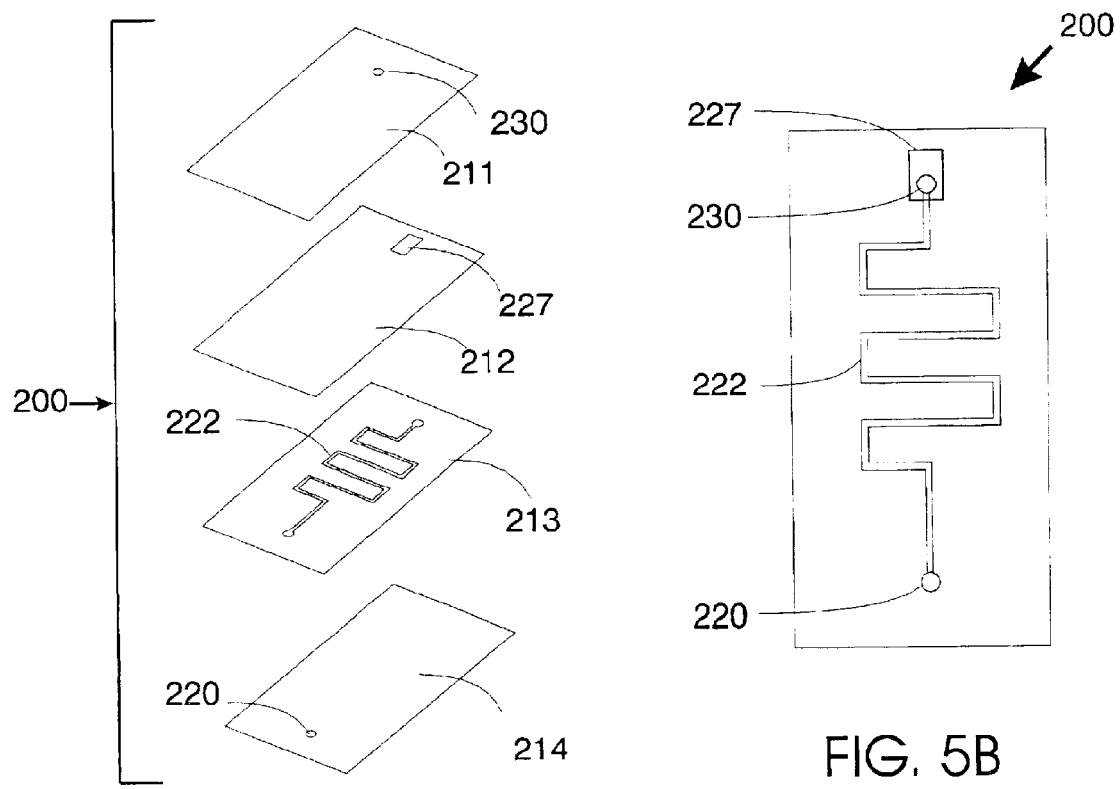
FIG. 5A
FIG. 5B
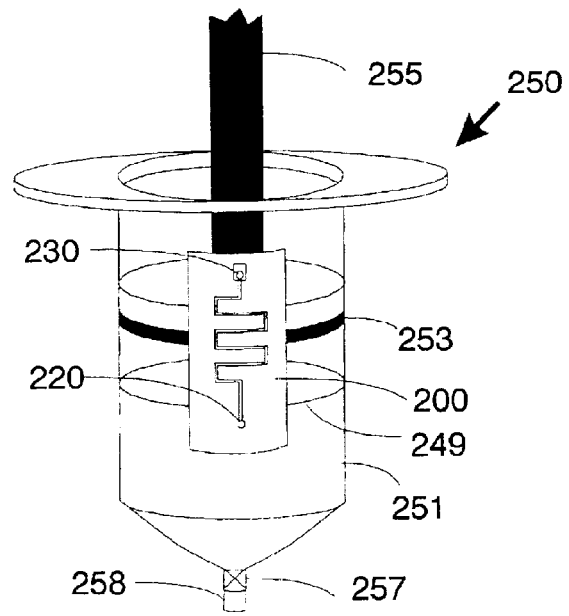
FIG. 5C

NON-PLANAR MICROFLUIDIC DEVICES AND METHODS FOR THEIR MANUFACTURE

FIELD OF THE INVENTION

The present invention relates to non-planar microfluidic devices and methods for their use and manufacture. These devices are useful in various liquid-distribution devices and sensing applications.

BACKGROUND OF THE INVENTION

There has been a growing interest in the manufacture and use of microfluidic systems for the acquisition of chemical and biological information. In particular, microfluidic systems allow complicated biochemical reactions to be carried out using very small volumes of liquid. These miniaturized systems improve the response time of the reactions, minimize sample volume, and lower reagent cost.

Traditionally, these microfluidic systems have been constructed in a planar fashion using techniques that are borrowed from the silicon fabrication industry. Representative systems are described, for example, in some early work by Manz et al. (Trends in Anal. Chem. (1990) 10(5): 144–149; Advances in Chromatography (1993) 33: 1–66). In these publications, microfluidic devices are constructed by using photolithography to define channels on silicon or glass substrates and etching techniques to remove material from the substrate to form the channels. A cover plate is bonded to the top of this device to provide closure. Miniature pumps and valves can also be constructed to be integral (e.g., within) such devices. Alternatively, separate or off-line pumping mechanisms are contemplated.

More recently, a number of methods have been developed that allow microfluidic devices to be constructed from plastic, silicone or other polymeric materials. In one such method, a negative mold is first constructed, and plastic or silicone is then poured into or over the mold. The mold can be constructed using a silicon wafer (see, e.g., Duffy et al., Analytical Chemistry (1998) 70: 4974–4984; McCormick et.al., Analytical Chemistry (1997) 69: 2626–2630), or by building a traditional injection molding cavity for plastic devices. Some molding facilities have developed techniques to construct extremely small molds. Components constructed using a LIGA technique have been developed at the Karolsruhe Nuclear Research center in Germany (see, e.g., Schomburg et al., Journal of Micromechanical Microengineering (1994) 4: 186–191), and commercialized by MicroParts (Dortmund, Germany). Jenoptik (Jena, Germany) also uses LIGA and a hot-embossing technique. Imprinting methods in PMMA have also been demonstrated (see, Martynova et.al., Analytical Chemistry (1997) 69: 4783–4789) However, these techniques do not lend themselves to rapid prototyping and manufacturing flexibility. Additionally, the foregoing references teach only the preparation of planar microfluidic structures. Moreover, the tool-up costs for both of these techniques are quite high and can be cost-prohibitive.

The microfluidic devices described above are substantially planar. Planar microfluidic devices, however, are not well-suited to certain applications, such as interfacing with ordinary pipes, cylinders, and other bulk fluid conduits not characterized by flat, planar surfaces. For example, it would be desirable to couple a microfluidic device to a syringe, so as to permit a fluid sample to be introduced directly into the device without additional manipulation. Additionally, conventional microfluidic devices are rigid, rendering them ill-suited for applications where flexibility is desirable. As a result, the utility of conventional microfluidic devices is limited.

SUMMARY OF THE INVENTION

In one aspect of the present invention, an inexpensive and robust microfluidic device that is substantially non-planar in configuration is provided. In a separate aspect, a microfluidic device that is flexible, in whole or in part, may be contoured to a variety of non-planar substrates or surfaces while maintaining its functionality.

In another aspect of the invention, a non-planar microfluidic device can be comprised of various polymeric materials, combinations of different polymers, and hybrids of polymeric and other materials such as silicon or glass. Metals and metallic films may also be used.

In a separate aspect of the invention, a microfluidic device comprises one or more stencils sandwiched between substrates. Preferably, the mating surfaces of the substrates are complementary so as to enable a seal with the sandwiched stencil to be formed. Preferably, the mating substrates appear planar during manufacture but may be contoured to various non-planar surfaces. The substrates may be stacked or layered to provide complex microfluidic device geometries having various internal channels. The substrate and stencil layers may all be flexible to permit construction of flexible devices.

In another separate aspect of the invention, a microfluidic device is contoured to a vessel (such as a pipe or section of tubing) that has fluid flowing through the pipe or tubing. Fluidic communication between the contents of the vessel and the microfluidic channels is established with a physical interface. Preferably, a flexible microfluidic device having a port physically contacts a pipe or tube having a radial aperture, with the port aligned to the aperture, to permit fluid to be introduced into or sampled by the device through the aligned port/aperture combination. This sampling can be either continuous or metered.

In another separate aspect of the invention, a nonplanar microfluidic device is removably attached to a vessel with a non-permanent adhesive, preferably a self-adhesive tape. In another separate aspect of the invention, a microfluidic device is contoured to connect to a syringe. Fluid may be exchanged between a syringe and a microfluidic device, advantageously by physically contacting the device to the syringe and aligning an aperture in the syringe with an inlet port in the microfluidic device. Such fluid exchange may, for example, permit fluid contents within the syringe to be sampled, either continuously or by metered sampling. Motion of the syringe plunger may be used to drive the fluidic motion within the microfluidic device. In another separate aspect of the invention, a microfluidic device is contoured to connect to other vessel types, such as a vial or container.

In another separate aspect of the invention, a continuously wrapped microfluidic device may be constructed from a single flexible material layer, and then wrapped either around itself or a vessel to form a completed device. In another separate aspect of the invention, a rewindable microfluidic device may be wrapped or unwrapped from around itself or a vessel, and still maintain the integrity of any fluidic sample contained by the device.

In another separate aspect of the invention, a syringe having multiple internal plungers permit fluid to be transferred to an associated chamber, such as a chamber located in an adjacent microfluidic device, to be filled on the draw stroke of the syringe.

In another separate aspect of the invention, a microfluidic device connects to a vessel having a continuously flowing fluid, the device being connected to the vessel both upstream and downstream of a pressure-reducing device located in the vessel.

In another separate aspect of the invention, methods of transferring fluid between a vessel and a microfluidic device are provided.

In a further aspect, any of the foregoing separate aspects may be combined for additional advantage.

Definitions

The term "channel" or "chamber" as used herein is to be interpreted in a broad sense. Thus, it is not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-Express through cell where fluid is to be continually passed or, alternatively, a chamber for holding a specified, discrete amount of fluid for a specified amount of time. "Channels" and "chambers" may be filled or may contain internal structures comprising valves or equivalent components.

The term "microfluidic" as used herein is to be understood, without any restriction thereto, to refer to structures or devices through which fluid(s) are capable of being passed or directed, wherein one or more of the dimensions is less than 500 microns. Additionally, such devices can be constructed using any of the materials described herein, as well as combinations of such materials and similar or equivalent materials.

The term "flexible" as used herein means able to endure strain, particularly due to being bent, folded, or stretched, without breaking or suffering permanent injury. "Flexible" as used herein may or may not further include the properties of being resilient or elastic.

The term "substantially non-planar" as used herein refers to the characteristic of not lying or being formed to necessarily lie within a single plane, at least in substantial part. In other words, a non-planar device according to the present invention may be a rigid device that is manufactured so as not to lie within a single plane, or may be a flexible device that appears to be substantially planar during manufacture but can be contoured or adapted to a non-planar surface. A "substantially non-planar surface" includes a curved surface, such as along the periphery of a cylinder, cone, or sphere, or a compound surface region such as a corner along the intersection of two planar or non-planar surfaces. In preferred embodiments according to the present invention, microfluidic devices are adapted to interface with (e.g., attach to) curved surfaces or compound surface regions, particular vessel surfaces.

The term "vessel" as used herein is to be interpreted in a broad sense. It is intended to refer not only to a container for holding a fluid (including liquids and/or gases), but also to a tube or canal (akin to an artery) in which a fluid is contained and conveyed. Examples of vessels to which microfluidic devices of the present invention may be attached include, but are not limited to, pipes, tubes (including flexible tubing), vials, syringes, tanks, bladders, and other containers with cylindrical, spherical, or curved portions.

The phrase "adaptably attached" as used herein refers to an interaction that may be adjusted or tailored to changing circumstances. An adaptable attachment typically involves contouring to a non-planar surface, which contouring may be performed either during or after manufacture of a device. An adaptable attachment may, but does not necessarily, include interaction between flexible or pliable components.

BRIEF DESCRIPTION OF THE DRAWINGS

In the figures, wherein like numbers denote elements with similar function:

FIGS. 2A, 2C, and 2E are exploded cross-sectional views of microfluidic devices illustrating various types of channel cross-sections that may be used in accordance with the current invention. FIGS. 2B, 2D, and 2F are assembled cross-sectional views of the devices of FIGS. 2A, 2C, and 2E, respectively.

FIG. 3A is a perspective view of a fluid-containing vessel having two radial apertures. FIG. 3B is an exploded perspective view of microfluidic device having flow regulation capability. FIG. 3C is a side perspective view of the (assembled) microfluidic device of FIG. 3B, flexed to adapt to a curved surface. FIG. 3D is a side perspective view of the of the microfluidic device of FIGS. 3B–3C contoured to the pipe of FIG. 3A.

FIG. 5A is an exploded perspective view of a microfluidic device that may be contoured to a syringe. FIG. 5B is a top view of the (assembled) microfluidic device of FIG. 5A. FIG. 5C is a perspective view of the microfluidic device of FIGS. 5A–5B contoured to a syringe.

DETAILED DESCRIPTION OF PREFERRED EMBODIMENTS OF THE INVENTION

Figure 1A:
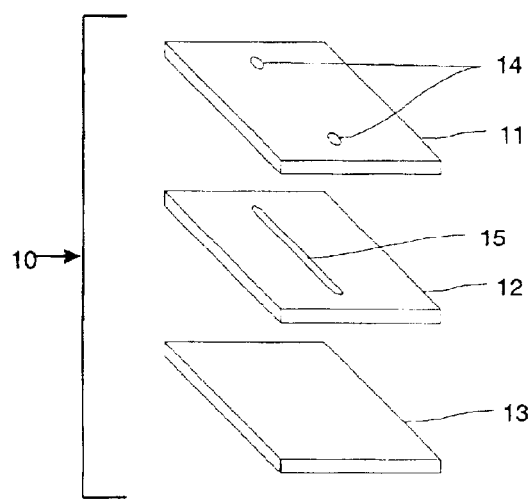
FIG. 1A is an exploded perspective view of a microfluidic device that can be contoured to a substantially non-planar configuration.

Non-planar microfluidic devices according to the present invention may be constructed in various ways. Preferably, such devices utilize stencils to define channels and/or chambers. Methods of and materials for constructing microfluidic devices useful with the present invention are provided in U.S. patent application Ser. No. 09/453,029 and in its counterpart application, WIPO international publication number WO 01/25138 (published Apr. 12, 2001) which are incorporated by reference herein as if reproduced in full. The devices disclosed therein comprise one or more stencils containing microstructures, which are disposed and sealed between substrate layers. The stencils can be constructed from any of various suitable materials, including preferably (but not limited to) Mylar®, polyester, polyimide and adhesive tape. Additionally, one or more materials may advantageously be used to coat, seal, and/or adhere the channels formed between the substrates. Coating material(s) may be used to coat the channels, seal the channels, and/or adhere the channels to adjacent layers of the device. In certain embodiments, the channels of the microfluidic devices may be fully or partially filled (e.g., using silk screening technology or mechanical placement of solid filters such as paper filters) during the manufacturing process. Use of various materials, including polymers, and coatings, provide for microfluidic devices that can accommodate the use of a wide range of liquid reagents or solutions. Maintaining contact between layers of a microfluidic device according to the present invention may be established by various chemical, mechanical, and physical means. For example, pressure-sensitive, hot-melt, and UV-curable adhesives or epoxies may be used. Alternatively, ultrasonic, thermal, or electromagnetic sealing techniques may be employed.

One notable advantage of microfluidic devices made with sandwiched stencils is that they may be rapidly prototyped with minimal tool-up costs, and manufactured at a relatively low cost, at both high and low production volumes. The stencils are preferably sandwiched between substrates, wherein the substrates may assume a planar configuration during manufacture. The substrates may be stacked or layered to provide complex microfluidic device geometries having various internal channels. Stencils are preferably self-adhesive to form a seal between adjacent substrates. Alternatively, an adhesive coating can be applied to stencil layers. Alternatively, the stencil layers may be held together using gaskets and/or mechanical force. Alternatively, applying heat, light or pressure can activate adhesion between layers.

Other manufacturing methods not relying on sandwiched stencils may be used to construct non-planar microfluidic devices according to the present invention. For example, non-planar devices may be constructed using molding, etching, or micromachining techniques with flexible or rigid materials. An example of a specific technique that may be used to produce non-planar devices according to the present invention is the silicone rubber replication technique discussed in Duffy et al., Analytical Chemistry (1988) 70:4974–4984. Rigid materials that could be used to construct nonplanar devices according to the present invention include, but are not limited to, silicon, glass, rigid polymers, and hybrids of polymers and other materials. However, when working with rigid materials to make non-planar microfluidic devices, using any of the techniques described herein, then extra care should be taken to ensure that the resulting devices will conform exactly to the target surface (s). Preferably, microfluidic devices according to the present invention are flexible, which aids in contouring such devices to interface with various surface shapes or surfaces that are subject to change in shape, such as pressurized bladders. Flexible materials useful with the present invention may be flexible along both the length and width of the device, or may be flexible only in one of the two directions, depending on requirements of the particular application. Preferably, neither bending nor deformation of a flexible nonplanar microfluidic device according to the present invention, nor placement of fluidic components added to a microfluidic device, inhibits the function of the device. Notably, devices according to the present invention may be pre-assembled and then applied to a vessel or surface, or they may be constructed in-field by sequentially applying layers of material directly to a vessel or surface.

The microfluidic devices described herein are preferably 'generic' in that they are modular and can be easily reconfigured into or adapted to any design. In addition, these devices are preferably capable of being used with a variety of pumping and valving mechanisms, including pressure, peristaltic pumping, electrokinetic flow, electrophoresis, vacuum and the like. In addition, microfluidic devices according to the present invention may be used in collaboration with optical detection (e.g., fluorescence, phosphorescence, luminescence, absorbance and colorimetry), electrochemical detection, and any of various suitable detection methods including visual detection. Suitable detection methods will depend on the geometry and composition of the device. The choice of such detection methods will be within the purview of the skilled artisan.

Figure 1B:
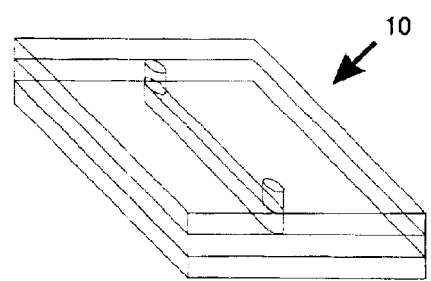
FIG. 1B is a perspective view of the (assembled) microfluidic device of FIG. 1A.

A preferred embodiment of the present invention is shown in FIGS. 1A–1B. Referring to FIG. 1A, a microfluidic device 10 is constructed from three material layers 11–13, all of which are made from one or more flexible material(s). Construction from flexible materials permits the device 10 to be deformed so as to contour to a non-planar surface, such as the exterior of a vessel. A channel 15 has been removed from the center material (stencil) layer 12, and inlet/outlet ports 14 have been removed from the top layer 11. The layers of material are brought together to form the assembled device 10 shown in FIG. 1B. The layers can be made of various materials, but once brought together must have some means for sealing the channels and holding the device together.

Cross-sectional views of microfluidic devices defining internal channels are shown in FIGS. 2A–2F. FIG. 2A shows three stencil layers 21–23 coming together to define a central microfluidic channel 25. When the layers are assembled, they form the completed device shown in FIG. 2B. In this particular embodiment, the cross section of the channel 25 is substantially rectangular or square, depending upon the width of the channel 25 and thickness of the center material layer 22. FIG. 2C is a cross sectional view of three nonplanar material layers 21A, 22A, 23A coming together to define a microfluidic channel 25A. These material layers 21A, 22A, 23A may be either flexible or rigid. FIG. 2D is a cross-sectional view of the assembled device 20A of FIG. 2C. Notably, FIG. 2D also bears the same configuration as would the device 20 of FIG. 2B if it were deformed due to downward flexure. That is, if the device 20 of FIG. 2B were to deformed due to downward flexure, the resulting cross section of the channel 25 would be the non-rectangular, polygonal shape of the channel 25A shown in FIG. 2D. In another embodiment of the invention having three material layers 31–33, as shown in FIG. 2E, the shape of the channel 35 prior to assembly is altered from a simple rectangular shape, so that when the device 30 is formed and flexed in order to contour to a given surface, the deformed channel 35 assumes a more rectangular cross-section, as shown in FIG. 2F. It is to be understood that numerous channel configurations other than those illustrated in FIGS. 2A–2F could be utilized in microfluidic devices within the scope of the present invention.

FIG. 3A shows a cylindrical vessel 50 suitable for attaching a microfluidic device. The vessel has two radial apertures 52, 54 that may be used for circulating fluid through a microfluidic device and returning it to the vessel. Preferably, as indicated by a flow direction arrow 55, the vessel 50 contains a continuously flowing fluid, such as a pipe segment utilized in a machine or industrial facility. For example, the vessel 50 may be part of a bioreactor device, such as are used to generate biological materials, including proteins. Microfluidic devices associated with the vessel 50 may be used for sensing various conditions, such as pressure, differential pressure, flow, temperature, pH, optical properties, or the presence of various chemicals or biological materials. Referring to FIGS. 3B–3C, a microfluidic device 100 having internal flow regulation capability is constructed from five material layers 111–115, all of which are made from one or more flexible materials. An inlet port 120 in the bottom layer 115 provides a fluid entry point to the device 100. Fluid flows through the channels 121, 125 and vias 120, 123, 126, 128 defined in the various layers, and exits the device 100 through an outlet port 130 in the bottom layer 115. Flow regulation capability is provided by virtue of the channel 121 intersecting channel 125 across the intermediate flexible layer 113. At low pressures and low flow rates, fluid within channel 121 exerts a relatively small outward force on, and does not deform, the flexible layer 113. However, as the pressure and flow rate raises, fluid within channel 121 exerts a large outward force on the flexible layer 113, causing it to deflect outward. At the intersection 124 of the channels 121, 125, outward deflection of the flexible layer 113 above channel 121 reduces the flow area of the channel 125, thus reducing its flow capability. In this manner, the device 100 serves to regulate flow within the microfluidic device 100.

Figure 4:
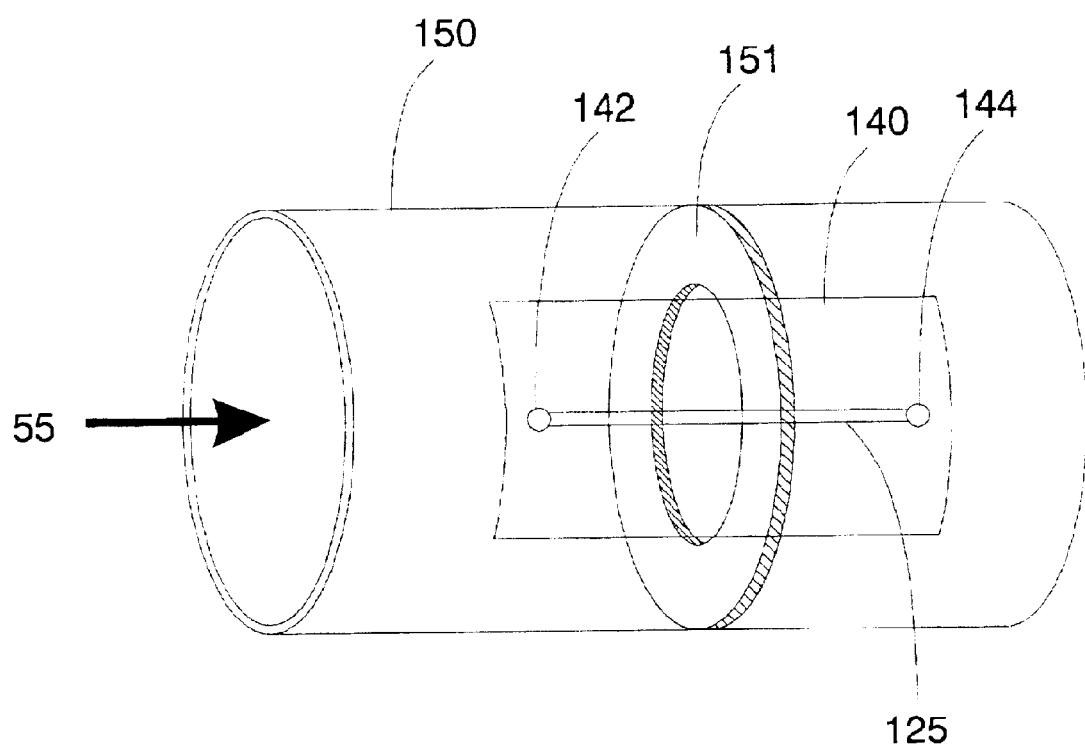
FIG. 4 is a perspective view of a microfluidic device contoured to the outside surface of a fluid-containing vessel having an internal orifice plate.

The device 100 may be fabricated from flat sheets of flexible material, as depicted in FIG. 3B, and then deformed into a non-planar shape as shown in FIG. 3C. Alternatively, a nonplanar device 100 such as shown in FIG. 3C may be formed from sandwiched layers of non-planar, rigid starting materials, from one or more non-planar molded or etched rigid layers, or combinations of these or other known fabrication techniques. Referring to FIG. 3D, the microfluidic device 100 of FIGS. 3B–3C is attached to the vessel 50 of FIG. 3A, the inlet port 120 being co-located with the first aperture 52 and the outlet port 130 being co-located with the second aperture 54 to facilitate fluidic exchange between the vessel 50 and the microfluidic device 100. Generally, fluid may be caused to flow in the presence of a pressure gradient, from regions of high pressure to low pressure. When a microfluidic device according to the present invention is attached to a vessel, fluid flow may be established by generating a pressure gradient between the device and the vessel. Such a pressure gradient may be established either by elevating the pressure in one region, decreasing the pressure in the other, or both. For example, a vessel may be pressurized or de-pressurized with a moveable piston and cylinder (such as a plunger within the vessel), or by connection to an external pressure or vacuum source. Alternatively, a microfluidic device according to the present invention may be connected to an external pressure or vacuum source to create a pressure gradient between a device and an associated vessel. Where a vessel contains a continuous fluid flow, one method of circulating flow through a microfluidic device having inlet and outlet ports in fluid communication with the vessel is to attach the microfluidic device with inlet and outlet ports positioned on either side of a pressure drop within the vessel, such as an orifice plate or other obstruction. For example, FIG. 4 illustrates a microfluidic device 140 having an inlet port 142 and outlet port 144 affixed to a vessel 150 having a first aperture, a second aperture, and an internal orifice plate 151, with the inlet and outlet ports 142, 144 of the microfluidic device 140 arranged on opposite sides of the orifice 151 and co-located with the first and second aperture, respectively. Having both the inlet and outlet ports 142, 144 of the microfluidic device 140 connected to the vessel 150 permits continuous sampling to be performed and helps to maintain the integrity of the bulk fluid, where maintaining such integrity is desirable.

In a preferred embodiment of the invention, a flexible microfluidic device is constructed to be mounted to a syringe or other vessel for gathering a fluidic sample. Referring to FIG. 5A, a microfluidic device 200 is constructed from four stencil layers 211–214, which include an inlet port 220, a channel 222, a porous membrane 227, and a vent 230. The assembled device 200 is shown in FIG. 5B. The device 200 can be contoured and mounted to a syringe having an external aperture co-located with an inlet port 220 of the microfluidic device 200. FIG. 5C shows the microfluidic device 200 of FIG. 5B coupled to a syringe 250, preferably by adhesive means. In a preferred embodiment, the stencil layer 214 is a non-permanent adhesive tape that adheres the microfluidic device to the syringe 250 but also permits the device 200 to be removed substantially intact from the syringe 250 when desired. Providing for removal from the syringe 250 allows a discrete sample to be extracted and collected in the microfluidic device 200, and then conveniently separated from the syringe 250. This may be desirable for processing or storing the discrete microfluidic sample separately from a bulk sample contained in the syringe 250.

In use, fluid 249 may be initially drawn from an external source (not shown) into the cavity 251 of the syringe 250 by retracting the plunger 255 from the syringe 250 through application of upward force on the stem 256. Outward movement of the plunger 255 creates a low-pressure region within the cavity 251. Once fluid 249 has entered the syringe cavity 251, the plunger 255 may be depressed in order to pressurize the cavity 251. Preferably, a valve 257 adjacent to the syringe inlet 258 is closed before or as the plunger 255 is depressed to aid in pressurizing the cavity 251. The valve 257 may be either a passive check valve or one that requires user intervention to operate. Assuming that the internal pressure of the attached microfluidic device 200 is lower than that within the vessel cavity 251, pressurization of the cavity 251 will cause fluid to flow through a radial aperture in the syringe 250, through the inlet port 220 in the microfluidic device 200 co-located with the radial aperture, and then into the microfluidic device 200. For fluid to flow into the microfluidic device 200, however, it must displace any initial contents of the device 200, typically (but not necessarily) air. To aid the flow of fluid into the microfluidic device 200, the device 200 preferably includes either an outlet port or a vent 230. If provided, an outlet port would allow fluid to fill the device 200 completely and overflow to another region, whether inside or outside the syringe. For example, an outlet port could permit overflow fluid to be conveyed to a collector or another modular microfluidic device. A vent 230, such as illustrated in FIGS. 5A–5C, is preferably coupled with a porous material 227 to inhibit passage of fluid but permit air or another gas to escape from the microfluidic device 200 as the gas is displaced by incoming fluid. The porous material 227 may define an entire layer of the device (such as layer 212), or, more preferably, may be confined to a limited region adjacent to the outlet aperture 230 such as by silk-screening or manually placing a pre-cut porous membrane in position. One example of a suitable air-permeable porous material is Gore-Tex®, although other materials that permit the passage of air but not liquid could be used. Additionally, a porous material within the microfluidic device 200 intended to absorb a fluid may be used to collect a discrete sample. As will be shown, hereinafter, many other configurations for coupling a syringe and microfluidic device may be utilized.

Figure 6A:
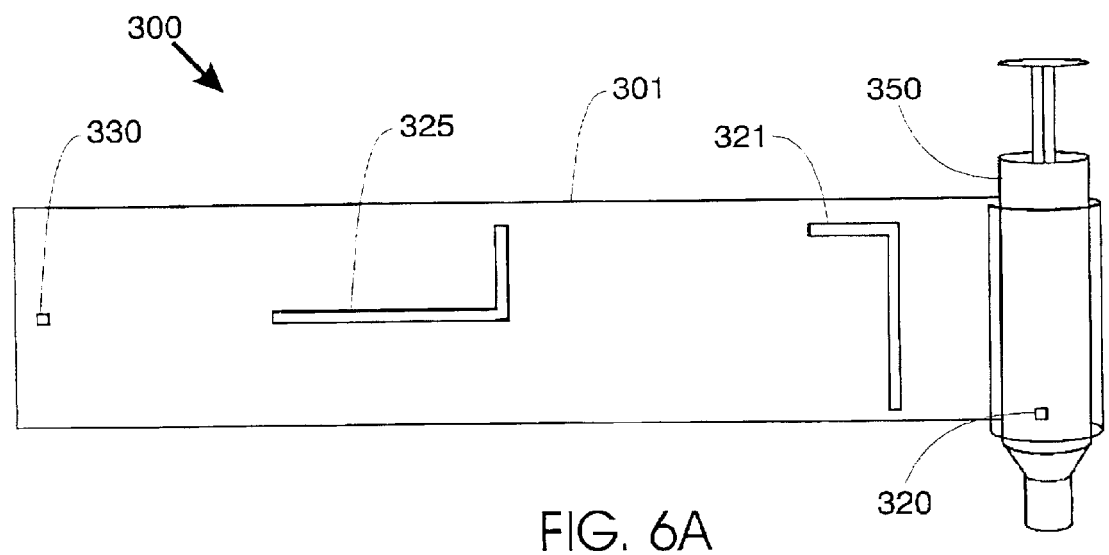
FIG. 6A is a perspective view of a continuous-form three-dimensional microfluidic device, adapted for use with and partially coupled to a syringe.
Figure 6B:
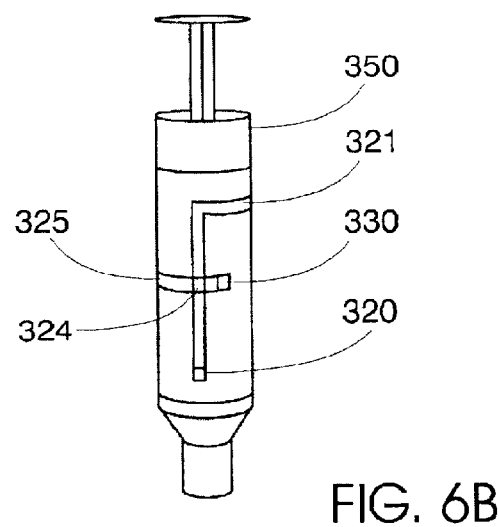
FIG. 6B is a perspective view of the (assembled) microfluidic device of FIG. 6A, adapted to and fully wrapped around a syringe.

When flexible materials are used, continuously-wrapped microfluidic devices according to the present invention may be constructed, providing significant fabrication efficiency. Various channels, vias, and functional devices including, for example, mixers and filters, may be defined in or filled into a single layer of polymer. The single layer of polymer may then be fashioned into a three-dimensional device by folding or wrapping the polymeric layer around itself, or by wrapping the polymeric layer around a vessel such as a cylinder. Referring to FIGS. 6A–6B, a microfluidic device 300 is constructed from a single flexible layer 301 by cutting various channels 321, 325 and apertures 320, 330 from the layer 301. Preferably, the layer 301 is polymeric and self-adhesive on one or both sides. Alternatively, liquid adhesives or other sealing means (such as disclosed in U.S. patent application Ser. No. 09/453,029) may be used to ensure the fluidic integrity of the device 300 when closed either upon itself or around a vessel. The particular device illustrated in FIG. 6A functions as a flow regulator, identical in operation to the flow regulator described in connection with FIGS. 3B–3C. Two channels 321, 325 in the microfluidic device 300 cross at an intersection 324 across an intermediate flexible layer, which is the continuously wrapped single layer 301 of the device 300. When the flow rate and pressure are low, relatively little force is exerted by one channel 321 against the intermediate flexible material 301 forming the boundary between the two channels at the channel intersection 324. As the flow rate and pressure rise, however, a higher force is exerted against the flexible material 301 along the boundary, thus causing the flexible material 301 to deflect and reduce the flow area of the other channel 325 at the intersection. In this manner, flow may be regulated within the microfluidic device 300. Wrapping the device 300 around a vessel, which in this example is a syringe 350, completes fabrication of the device 300. FIG. 6B illustrates the assembled combination, with the device 300 completely wrapped around the syringe 350.

Figure 7A:
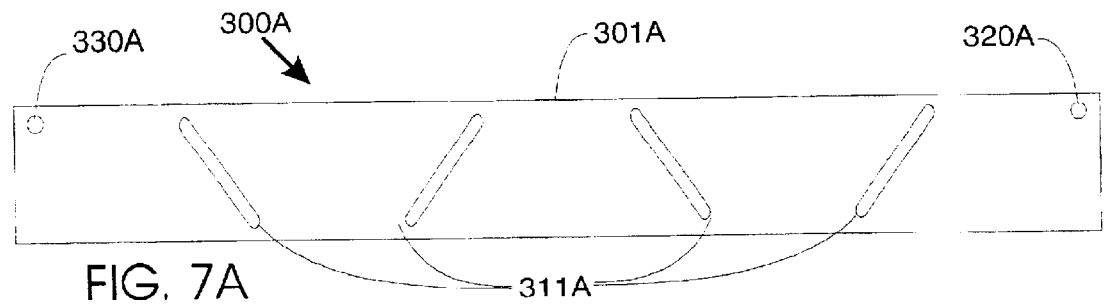
FIG. 7A is a front view of a continuous-form three-dimensional microfluidic device, adapted for use with a fluid conduit.
Figure 7B:
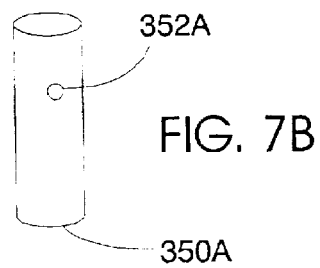
FIG. 7B is a perspective view of a cylindrical fluid conduit having a radial aperture.
Figure 7C:
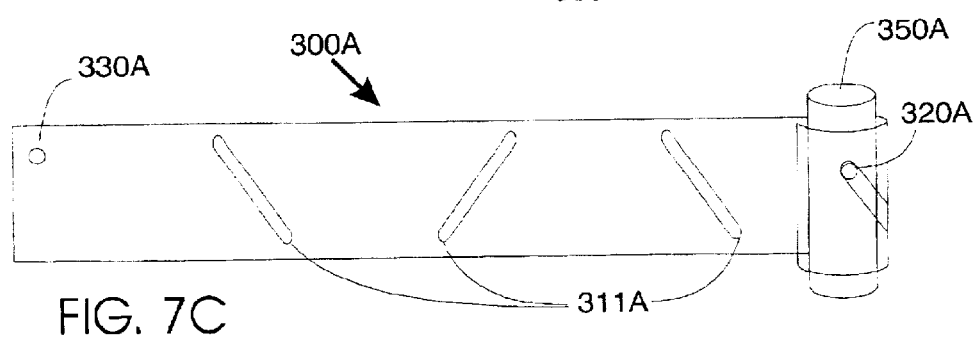
FIG. 7C is a perspective view of the microfluidic device of FIG. 7A, partially coupled to the fluid conduit of FIG. 7B.
Figure 7D:
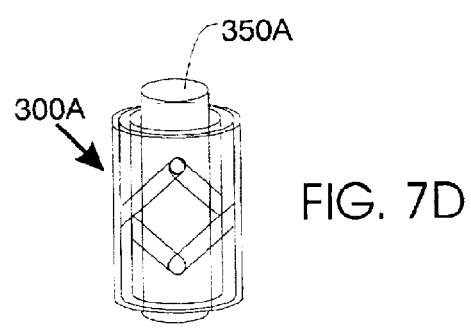
FIG. 7D is a perspective view of the microfluidic device and fluid conduit of FIG. 7C, wherein the device is fully wrapped around the fluid conduit.

Referring to FIGS. 7A–D, a microfluidic device 300A forming a very long composite channel is constructed by removing angled channels 311A from a single layer of flexible material 301A and wrapping the layer 301A around a cylindrical vessel 350A so that the angled channels 311A overlap. The spacing between the channels 311A on the flat sheet 301A is advantageously equal to the circumference of the cylinder 350A plus the thickness of any portion of the sheet 301A already wrapped to the cylinder 350A. FIG. 7B shows a cylindrical vessel 350A having a radial aperture 352A defined therein. The flexible material layer 301A defines an inlet port 320A and an outlet port 330A, and the inlet port 320A is preferably co-located with the aperture 352A to permit fluid to flow between the vessel 350A and the device 300A. When the device 300A is fully wrapped, such as shown in FIG. 7D, an outlet port 330A defined in the flexible material layer 301A permits an interface between the microfluidic device 300A and other systems. For example, the device 300A may be connected to an external reservoir (not shown) by way of the outlet port 300A, or a porous membrane (not shown) may be associated with the outlet port 330A to function as a vent.

Figure 8A:
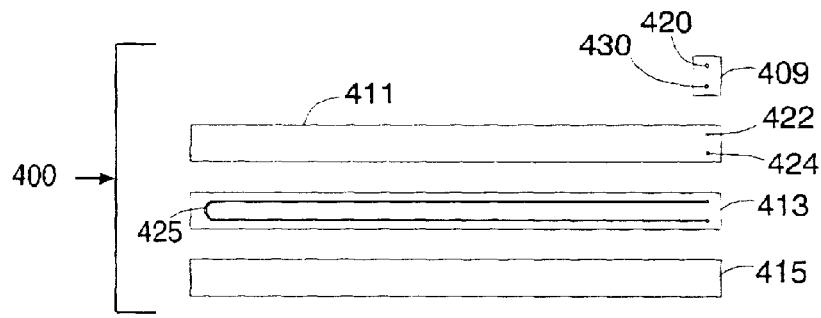
FIG. 8A is an exploded side view of a rewindable flexible microfluidic device according to the present invention.
Figure 8C:
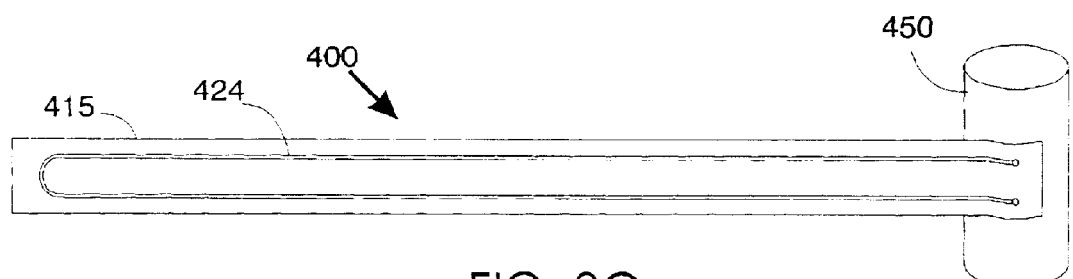
FIGS. 8C–8D are perspective views of the device of FIG. 7A mated with the conduit of FIG. 7B, in unwound and wound conditions, respectively.
Figure 8D:
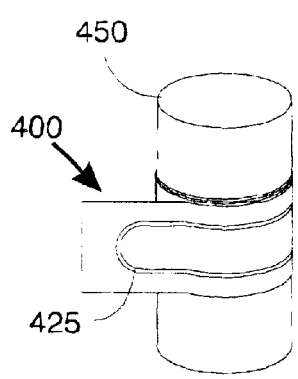
Figure 8B:
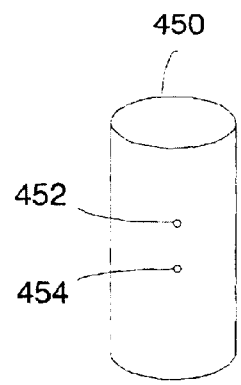
FIG. 8B is a perspective view of a cylindrical fluid conduit having two radial apertures.

A different continuously wrapped microfluidic device 400 is shown in FIGS. 8A–8C. While initially similar in appearance to the embodiment shown in FIG. 7D, the device 400 includes internal and external cover layers 411, 415 that sandwich at least one stencil layer 413, thus maintaining the integrity of a fluid sample contained within while permitting the device 400 to be alternately wound or unwound about the exterior of a vessel 450 having apertures 452, 454. Preferably, the cover layers 411, 415 are joined to any intermediate stencil layers such as stencil layer 413 with adhesives or self-adhesive layers. For example, stencil layer 413 may be a double-sided adhesive material, with layers 411 and 415 being ordinary (non-adhesive) film. Preferably, the microfluidic device 400 attaches to the vessel 450 with a double-sided adhesive layer 409 that extends along only a portion of the length of the device 400. The adhesive layer 409 has inlet and outlet ports 420, 430 to permit fluid to enter and exit the device 400. Within the device 400, fluid flows through apertures 422, 424 and a channel 425. As an alternative to the adhesive layer 409, the microfluidic device 400 may be attached to the vessel 450 by other chemical, mechanical, or physical means that would be recognized by one skilled in the art. In a further alternative, the microfluidic device 400 may be attached to the vessel 450 along a portion of the internal cover layer 411 without an intermediate adhesive layer 409. Providing the capability to be alternately wound and unwound permits a large microfluidic device to be conveniently attached to and packaged with a vessel such as a syringe. That is, the length and surface area of the device 400 when unwound from the vessel 450 may far exceed the circumference and corresponding surface area of the vessel 450, permitting interaction with complex microfluidic devices. The simple microfluidic channel 425 shown in FIGS. 8A–8D transports fluid within the device 400 from a first port 420 to a second port 430, which are aligned with apertures 452, 454, respectively, in the vessel 450 to permit fluid to be introduced into the device 400 and to be returned to the vessel 450. Alternatively, an external port or vent, such as shown in FIGS. 5A–5C may be substituted for the co-located second port and second aperture. Such an external port or vent may be advantageously placed along the distal end 416 of the external cover 415 to preserve the functionality of the external port or vent when the device 400 is wound around the vessel 450. While only a simple channel configuration is provided in the device 400, more complex devices and channels facilitating various functions are contemplated.

Figure 13A:
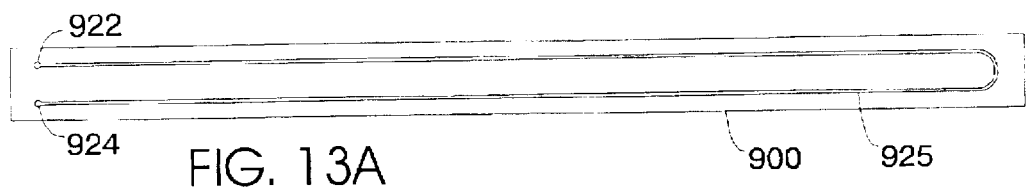
FIG. 13A is a side view of a rewindable microfluidic device.
Figure 13B:
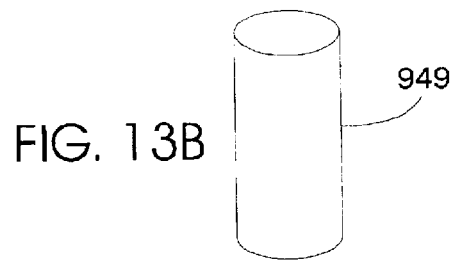
FIG. 13B is a perspective view of a rod about which the microfluidic device of FIG. 13A may be wrapped.
Figure 13C:
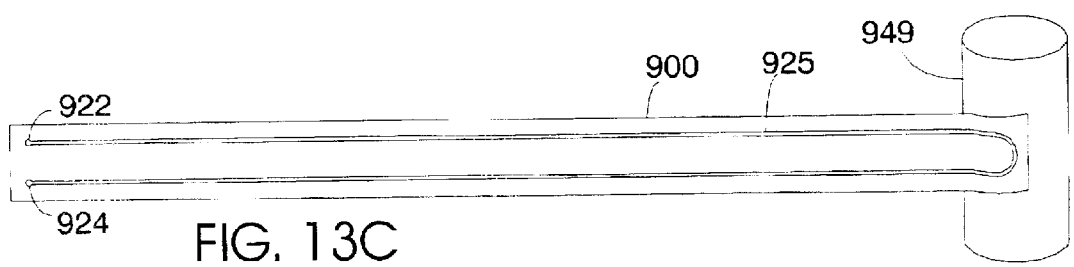
FIG. 13C is a perspective view of the rewindable microfluidic device of FIG. 13A placed against the rod of FIG. 13B.
Figure 13D:
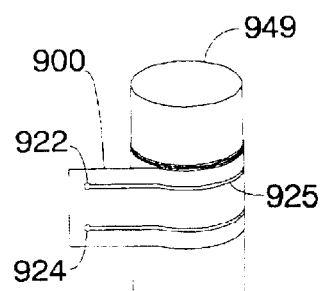
FIG. 13D is a perspective view of the rewindable microfluidic device of FIG. 13A substantially wrapped around the rod of FIG. 13D.
Figure 13E:
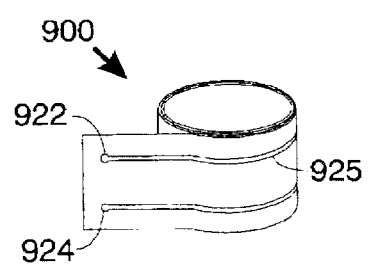
FIG. 13E is a perspective view of the microfluidic device of FIG. 13D wrapped about itself to form a roll.

Referring to FIGS. 13A–13E, a rewindable flexible microfluidic device 900 similar to the device 400 shown in FIG. 8A may be wound without affixing the device 900 to a vessel. The device 900 is preferably constructed from one or more central stencil layer(s) sandwiched between flexible cover layers defining inlet and outlet apertures 922, 924 providing access to at least one microfluidic channel 925 within the device 900. Following construction of the device 900, it may be rolled or wound around a rod 949, such as shown in FIGS. 13C–13D. Notably, the inlet and outlet ports 922, 924 of the device 900 are located at the distal end of the device 900, permitting these ports 922, 924 to be easily accessed when the device 900 is coiled. After the device 900 is wound around the rod 949, the rod 949 may be removed to yield a coiled microfluidic device 900 resembling a roll of film, such as shown in FIG. 13E. As the length of the microfluidic device 900 may far exceed the circumference of the rod 949, at least one very long channel 925 may be defined in a very compact volume when the device 900 is coiled. Long channels (such as illustrated in FIGS. 7D, 8C, and 13E) may be incorporated into other devices, such as, for example, an elongated microfluidic electrokinetic separation device. In operating such a separation device, the channel(s) 925 may be filled with a separation buffer and subjected to electric fields by electrodes (not shown) positioned at various locations, such as along the inlet and outlet ports 922, 924. Implementation of utilitarian electrokinetic (also termed "electrophoretic) devices are known in the art, with details provided, for example, in references such as U.S. Pat. No. 5,750,015 and No. 5,858,195.

Figure 9A:
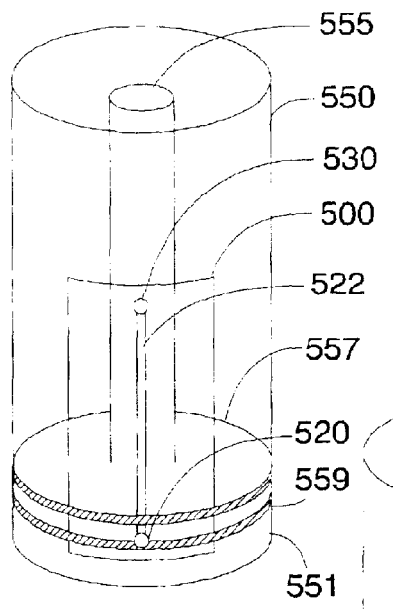
FIGS. 9A–9C are perspective views of a three-dimensional microfluidic device coupled with a cylindrical vessel having multiple internal plungers, the plungers being illustrated at various stroke positions.
Figure 9B:
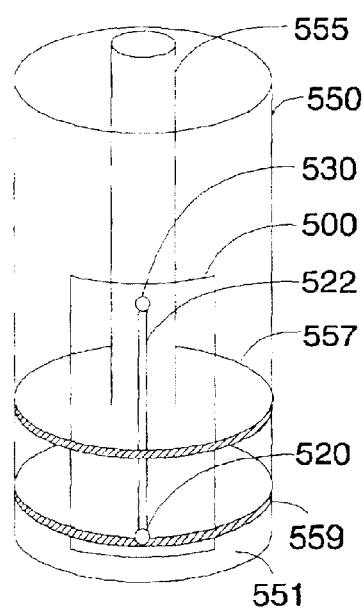
Figure 9C:
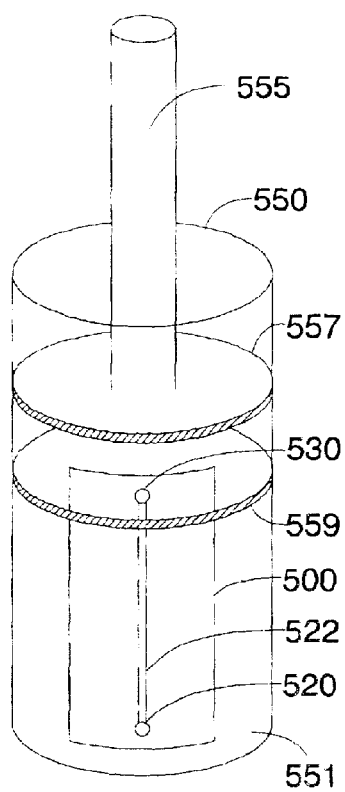

Referring to FIGS. 9A–9C, a further embodiment includes a microfluidic device 500 coupled with a syringe 550 having multiple plungers 557, 559 to facilitate introduction of fluid into the microfluidic device 500 on the outward (draw) stroke of the syringe stem 555. The microfluidic device 500 preferably has two apertures in the syringe 500 co-located with inlet and outlet ports 520, 530, respectively, in the microfluidic device 500. The microfluidic device 500, which is preferably composed of sandwiched stencils, further has a microfluidic channel 522 connecting the inlet and outlet ports 520, 530. Although somewhat similar to the coupled microfluidic device and syringe embodiment shown in FIG. 5C, the inclusion of multiple plungers 557, 559 in the present embodiment facilitates different interaction between the syringe 550 and the device 500. The plungers 557, 559, which are sealingly engaged to the inner surface of the syringe 550, may or may not be mechanically linked to one another. In operation, the upper plunger 557 is drawn upward by the stem 555, creating a low-pressure region between the first and second plungers 557, 559. The lower plunger 559 may be drawn upward due to vacuum action caused by relative motion of the upper plunger 557, or by a mechanical link (such as shown in FIGS. 12A–12C and FIGS. 11A–11C, respectively) connecting the two plungers 557, 559 within the syringe 550. Motion of the lower plunger 553 within the syringe 550 creates a low-pressure region that draws fluid into the syringe cavity 551 from an external source (not shown). Whenever the outlet port 530 of the microfluidic device 500 is positioned between the first and second plungers 557, 559, the inlet port 520 is submerged in fluid in the cavity 551, and region between the plungers 557, 559 is at a lower pressure than the cavity 551, then fluid will flow into the microfluidic device 500 from the inlet port 520 toward the outlet port 530.

Figure 10A:
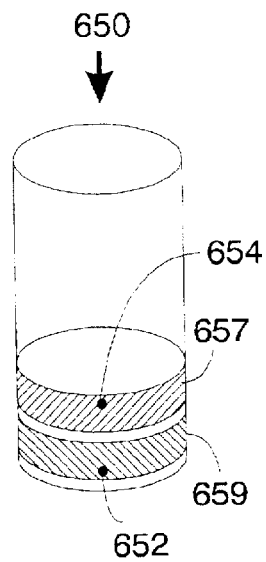
FIGS. 10A–10D are perspective views of a portion of a simplified syringe having two apertures and two plungers, showing various initial positions for plungers relative to the apertures.
Figure 10B:
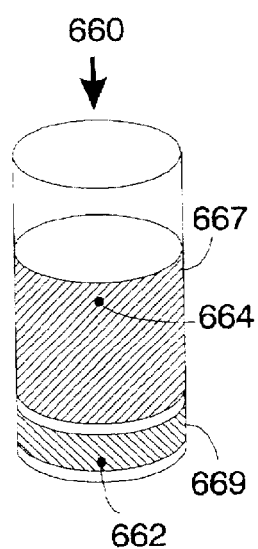

Various initial configurations of plungers relative to radial inlet and outlet apertures in multi-plunger syringes, each providing different results during use, are shown in FIGS. 10A–10D. In each of these Figures, it is assumed that the plungers are capable of movement, such as if the upper plungers were connected to a syringe stem (not shown), and the upper and lower plungers in each syringe may or may not be mechanically linked. It is to be further assumed that the upper and lower aperture in each syringe embodiment is in fluidic communication, such as by connection to a microfluidic device or other fluidic system. Referring to FIG. 10A, a simplified syringe 650 has two plungers 657, 659 and two apertures 652, 654. In an initial position, the lower plunger 659 is positioned along the level of the lower aperture 652, and the upper plunger 657 is positioned along the level of the upper aperture 654. In operation, the upper plunger 657 would move first, until suction (and/or a mechanical link such as shown in FIGS. 11A–11C) between the plungers 657, 659 causes the lower plunger 659 to move, which would draw fluid from an external source (not shown) into the syringe 650. The upper plunger 657 would move past the upper aperture 654 shortly after the fluid begins to enter the syringe 650. As soon as the upper aperture 654 is positioned between the two plungers 657, 659, then fluid flows from the primary syringe cavity (below the lower plunger 659) through the lower aperture 652, outside the syringe 650, and toward the upper aperture 654. Because the upper plunger 654 initially covers the upper aperture 654, there would be no air transfer from above the upper plunger 654 into the primary syringe cavity. FIG. 10B illustrates the same basic idea as FIG. 10A (namely, a simplified syringe 660 with a lower plunger 669 initially positioned along the level of a lower aperture 662, and an upper plunger 667 initially positioned along the level of the upper aperture 664) but with a thicker upper plunger 667, which would allow for a greater volume of fluid to be drawn into the syringe cavity below the lower plunger 669 before fluid is motivated to be drawn through the lower aperture 662, outside the syringe 660, and toward the upper aperture 664.

Figure 10C:
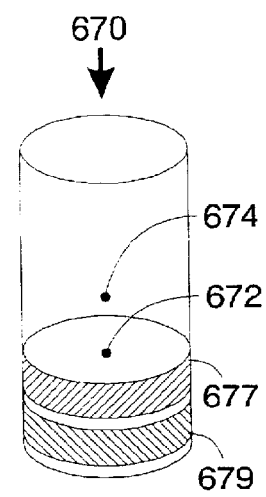
Figure 10D:
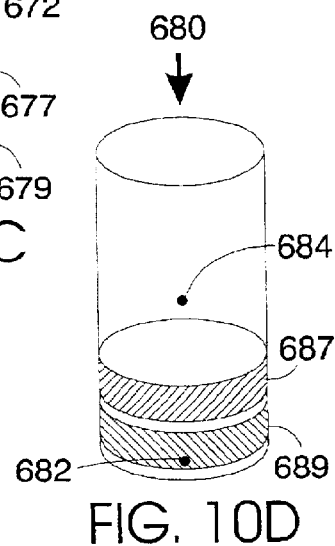
Figure 11A:
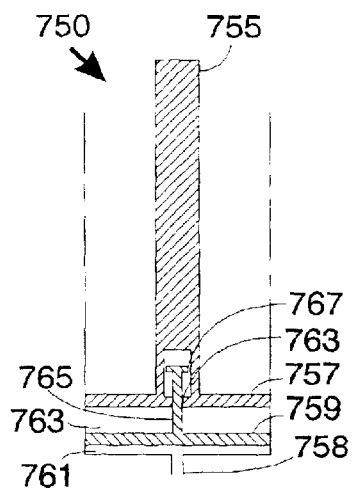
FIGS. 11A–11C are side sectional views of a cylindrical vessel having multiple internal plungers mechanically linked to one another, the plungers being illustrated at various stroke positions.
Figure 11B:
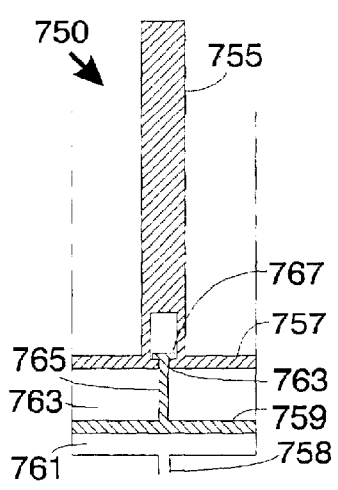
Figure 11C:
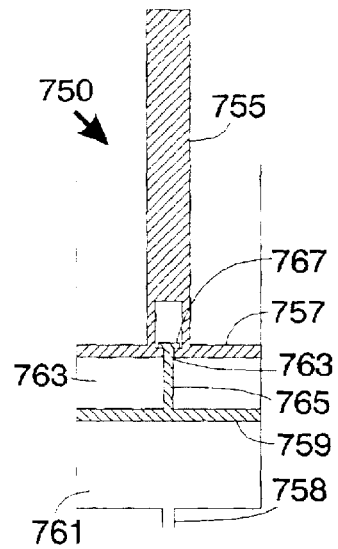

FIG. 10C illustrates a simplified syringe 670 with two plungers 677, 679 both positioned below two apertures 672, 674. As soon as the upper plunger is drawn past the lower aperture 672, air can be drawn into the region between the two plungers 677, 679. If the plungers are not mechanically linked, and air enters the region between the two plungers 677, 679 at a fast enough rate, then the air leakage may stop the motion of the lower plunger 679. Otherwise, air leakage will merely slow the motion of the lower plunger 679 until the upper plunger 677 passes the upper aperture 674, which would stop air transfer into the region between the plungers 677, 679. As soon as the lower plunger 679 moves past the lower aperture 672, fluid would be motivated to pass through the lower aperture 672, outside the syringe 660, and toward the upper aperture 674, until such time as the lower plunger 679 moves past the upper aperture 674. Referring to FIG. 10D, a simplified syringe 680 has two plungers 687, 689, one positioned along the level of a lower aperture 682, and the upper plunger 687 positioned well below an upper aperture 684. In this embodiment, assuming that the upper aperture 684 is vented to atmosphere, motion of the upper plunger 687 would create a low pressure region between the two plungers 687, 689 that is capable of drawing the lower plunger 689 upward, thus creating a low pressure region in the primary syringe cavity below the lower plunger 689. Once the lower plunger 689 moves to expose the lower aperture 682, assuming that the upper and lower apertures 684, 682 are in fluid communication through an external device (not shown), then air will be motivated to flow into the syringe cavity below the lower plunger 689 as liquid is also drawn into the primary syringe cavity. This air leakage would proceed until such time as the upper plunger 687 moves past the upper aperture 684. At that point, fluid would be motivated to flow from the cavity below the lower plunger 689, through the lower aperture 682 outside the device 680 and toward the upper aperture 684 even as fluid continues to flow into the primary cavity of the syringe 680 below the lower plunger 682.

It is notable to mention that the particular operation of devices according to FIGS. 10A–10D depends on the flow rate through the external devices (such as microfluidic devices) connecting the apertures of each syringe, relative to the fluid flow rate into each syringe cavity. The foregoing discussion of this operation is intended to exemplify potential operational modes. Additionally, the upper aperture in each syringe 650, 660, 670, 680 could be vented to fluids (including inert gases) other than air.

Referring to FIGS. 11A–11C, a multi-plunger vessel 750 has an upper plunger 757 that is mechanically coupled to a lower plunger 759. The vessel 750 may be, but is not limited to being, a syringe. Additionally, the term "plunger" may be used interchangeably with the term "piston" herein. A main stem 755 linked to the upper plunger 757 permits movement of the upper plunger 757. The lower plunger 759 has a secondary stem 765 projecting through a collar 763 in the upper plunger 757, with a flared tip 767 sized to catch the collar 763 as the upper plunger 757 moves upward. Other types and configurations of mechanical linkages between the plungers 757, 759 could be used. In operation, upward movement of the main stem 755 draws the upper plunger 757 upward. Since the upper plunger is sealingly engaged against the interior of the vessel 750, relative movement between the two plungers 757, 759 creates a low-pressure region in the secondary cavity 763 between the two plungers 757, 759. When the upper plunger 757 proceeds upward a distance equal to the length of the secondary stem 765 (i.e., the deadband length), the flared tip 767 catches the collar 763 to draw the lower plunger 759 upward. Thereafter, upward motion of the main stem 755 draws both plungers 757, 759 upward equally, creating another low-pressure region in the primary cavity 761 below the lower plunger 759 capable of drawing a fluid into the cavity 761. Adjusting the thicknesses and placement of the plungers 757, 759 relative to any apertures in the vessel 750, such as illustrated in FIGS. 10A–10D, permits fluid to be introduced through the vessel inlet 758, with or without air, into a chamber (such as a microfluidic device) external to the vessel 750 during the upward (draw) stroke of the main stem 755.

Figure 12A:
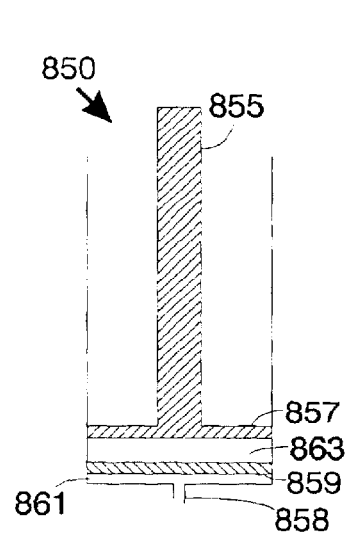
FIGS. 12A–12C are side sectional views of a cylindrical vessel having multiple internal plungers illustrated at various stroke positions.
Figure 12B:
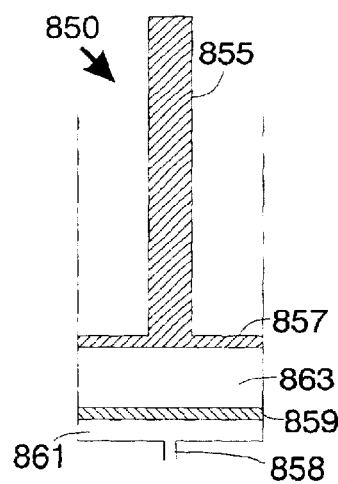
Figure 12C:
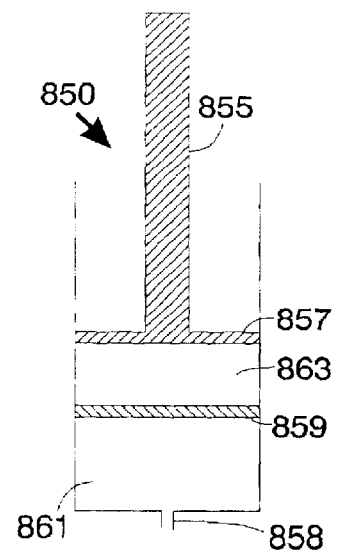

FIGS. 12A–12C provide a multi-plunger vessel 850 similar to the embodiment shown in FIGS. 11A–11C, except lacking a linkage between the upper and lower plungers 857, 859. Instead, the vessel 850 operates by utilizing a vacuum between the two plungers 857, 859. In operation, upward motion of a main stem 855 draws the upper plunger 857 upward, creating a low-pressure region in the secondary cavity 863 between the two plungers 857, 859. Since both plungers 857, 859 are sealingly engaged against the interior of the vessel 850, the vacuum in the secondary cavity 863 will eventually cause the lower plunger 859 to be drawn upward. Upward motion of the lower plunger 859 will then create a low-pressure region behind the lower plunger 859 in the primary cavity 861 capable of drawing fluid into the cavity 861 from an external source (not shown) through a vessel inlet 758. As above, depending on configuration, the vessel 850 can provide the same utility as the vessel 750 depicted in FIGS. 11A–11C. Thus, novel vessels (including syringes) having multiple plungers and capable of transferring fluid between a vessel and an external device (including a microfluidic device) are provided.

The particular devices, construction methods, and fluid manipulation methods illustrated and described herein are provided by way of example only, and are not intended to limit the scope of the invention, which should be restricted only in accordance with the appended claims and their equivalents.

What is claimed is:

1. A system for transferring fluid between a vessel and a microfluidic device, the system comprising:

a vessel capable of holding a fluid, the vessel having at least one substantially nonplanar external wall defining a first aperture therein;

wherein the vessel includes a substantially cylindrical portion having a central axis, the at least one substantially nonplanar external wall bounds the substantially cylindrical portion, and the first aperture is disposed substantially perpendicular to the central axis; and a microfluidic device having a first port;

wherein the microfluidic device is adaptably attached to the vessel by co-locating the first port with the first aperture such that fluid can flow between the vessel and the microfluidic device through the co-located first aperture and first port.

2. The system of claim 1 wherein the microfluidic device is flexible.

3. The system of claim 1 wherein the microfluidic device is made with sandwiched stencils.

4. The system of claim 3 wherein at least one stencil is made of a polymeric material.

5. The system of claim 3 wherein the microfluidic device includes multiple layers, and at least one layer is a self-adhesive tape.

6. The system of claim 5 wherein at least one layer of self-adhesive tape is self-adhesive on both sides.

7. The system of claim 5 wherein the microfluidic device adaptably attaches to the vessel with self-adhesive tape.

8. The system of claim 1 wherein following attachment the microfluidic device may be removed substantially intact from the vessel.

9. The system of claim 1 wherein fluid flows from the vessel into the microfluidic device.

10. The system of claim 1 wherein fluid flows from the microfluidic device into the vessel.

11. The system of claim 1 wherein the vessel contains a continuous flow of fluid.

12. The system of claim 1 wherein the microfluidic device has a vent.

13. The system of claim 12 wherein the vent is an air-permeable membrane that inhibits the passage of liquid.

14. The system of claim 1 wherein the microfluidic device has a second port such that fluid can flow within the microfluidic device from the first port to the second port.

15. The system of claim 14, wherein a second aperture is defined in an external wall of the vessel, and the second port is co-located with the second aperture such that fluid can flow between the vessel and the microfluidic device through the co-located second port and second aperture.

16. The system of claim 1 wherein the vessel is selected from the group consisting of: a pipe, a tube, a vial, and a syringe.

17. The system of claim 1 wherein the vessel is cylindrical and includes a moveable piston sealingly engaged therein.

18. The system of claim 1 wherein the microfluidic device comprises a stencil continuously wrapped around the vessel.

19. The system of claim 18 wherein the continuously wrapped stencil is self-adhesive.

20. The system of claim 18 wherein at least a portion of the vessel is cylindrical in shape.

21. The system of claim 18 wherein the vessel is a syringe.

22. The system of claim 1 wherein the microfluidic device is a rewindable flexible device.

23. The system of claim 22 wherein the microfluidic device is composed of sandwiched stencils.

24. The system of claim 23 wherein the device includes an internal cover layer and an external cover layer.

25. The system of claim 22 wherein the vessel has a circumference, the microfluidic device has a length, and the unwound length of the microfluidic device exceeds the circumference of the vessel.

26. The system of claim 1 wherein the microfluidic device is used to detect the presence of at least one chemical or biological material in the fluid.

27. The system of claim 1 wherein the microfluidic device is used to sense at least one physical property of the fluid.

28. The system of claim 27 wherein the at least one physical property is selected from the group consisting of: temperature, pressure, differential pressure, and flow.

29. The system of claim 11 wherein the vessel comprises a bioreactor vessel.

30. A method for transferring fluid between a vessel and a microfluidic device, the method comprising the steps of:
providing a vessel capable of holding fluid, the vessel having at least one substantially nonplanar external wall defining a first aperture therein;
wherein the vessel includes a substantially cylindrical portion having a central axis, the at least one substantially nonplanar external wall bounds the substantially cylindrical portion, and the first aperture is disposed substantially perpendicular to the central axis;
providing a microfluidic device having a first port and being adapted to contour to the vessel adjacent to the first aperture;
attaching the microfluidic device to the vessel such that the first port is co-located with the first aperture; and
causing fluid to flow between the vessel and the microfluidic device.

31. The method of claim 30 wherein fluid is caused to flow between the vessel and the microfluidic device by generating a pressure gradient between the vessel and the microfluidic device.

32. The method of claim 30, wherein the microfluidic device is flexible.

33. The method of claim 30 wherein the microfluidic device attaches to the vessel with an adhesive.

34. The method of claim 30 wherein the microfluidic device comprises a self-adhesive tape and wherein the microfluidic device attaches to the vessel with the self-adhesive tape.

35. The method of claim 30 wherein the microfluidic device is made with sandwiched stencils.

36. The method of claim 30 further comprising the step of venting any initial contents of the microfluidic device.

37. The method of claim 30 further comprising the step of removing the microfluidic device substantially intact from the vessel.

38. The method of claim 30 wherein fluid flows through the microfluidic device and at least a portion of the fluid is returned to the vessel.

39. The method of claim 30 wherein the microfluidic device has a second port such that fluid can flow within the microfluidic device from the first port to the second port.

40. The method of claim 39, wherein a second aperture is defined in an external wall of the vessel and the microfluidic device has a second port, the second aperture being co-located with the second port such that fluid can flow between the vessel and the microfluidic device through the co-located second aperture and second port.

41. The method of claim 30 wherein the vessel contains a continuous flow of fluid.

42. The method of claim 30 wherein the vessel is selected from the group consisting of: a pipe, a tube, a vial, and a syringe.

43. The method of claim 31 wherein the vessel is cylindrical and includes a moveable piston sealingly engaged therein.

44. A fluid sampling device comprising:
a cylindrical vessel capable of holding fluid, the vessel having a characteristic length and an interior wall that defines a first and a second radial aperture displaced from one another along the length of the vessel;
a first moveable plunger sealingly engaged to the interior wall of the vessel;
a second moveable plunger sealingly engaged to the interior wall of the vessel; and
a reservoir having an inlet port in fluid communication with the first aperture and having an outlet port in fluid communication with the second aperture;
wherein fluid is transferred from the vessel into the reservoir as the first and second plungers are translated outward from the vessel.

45. The device of claim 44, wherein the reservoir is a microfluidic reservoir.

46. The device of claim 45, wherein the microfluidic reservoir includes a microfluidic channel.

47. The device of claim 45, wherein the microfluidic reservoir is external to the vessel.

48. The device of claim 45, wherein the microfluidic reservoir is attached to the vessel.

49. The device of claim 44 wherein the first plunger and the second plunger are connected by a mechanical linkage.

50. The device of claim 48 wherein the mechanical linkage has a deadband.

51. The device of claim 44 wherein the first plunger and the second plunger are not physically connected.

52. The device of claim 44 wherein the vessel is a syringe.

\* \* \* \* \*